(12) United States Patent
Van Bommel et al.

(10) Patent No.: US 12,049,997 B2
(45) Date of Patent: Jul. 30, 2024

(54) LIGHT GENERATING DEVICE HAVING IMPROVED PERFORMANCE FOR DISINFECTION AND GENERAL LIGHTING

(71) Applicant: SIGNIFY HOLDING B.V., Eindhoven (NL)

(72) Inventors: Ties Van Bommel, Horst (NL); Olexandr Valentynovych Vdovin, Maarheeze (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/277,808

(22) PCT Filed: Feb. 14, 2022

(86) PCT No.: PCT/EP2022/053464
§ 371 (c)(1),
(2) Date: Aug. 18, 2023

(87) PCT Pub. No.: WO2022/175191
PCT Pub. Date: Aug. 25, 2022

(65) Prior Publication Data
US 2024/0142088 A1  May 2, 2024

(30) Foreign Application Priority Data

Feb. 18, 2021 (EP) .................... 21157804

(51) Int. Cl.
*F21V 9/32* (2018.01)
*A61L 2/08* (2006.01)
(Continued)

(52) U.S. Cl.
CPC .............. *F21V 13/08* (2013.01); *A61L 2/10* (2013.01); *A61L 2/26* (2013.01); *F21V 9/32* (2018.02);
(Continued)

(58) Field of Classification Search
CPC ... F21V 13/08; F21V 9/32; A61L 2/10; A61L 2/26
See application file for complete search history.

(56) References Cited

U.S. PATENT DOCUMENTS

| 5,436,919 A | 7/1995 | Chwalek et al. |
| 2007/0091949 A1 | 4/2007 | Adachi |

(Continued)

FOREIGN PATENT DOCUMENTS

CN  112268886 A  1/2021

OTHER PUBLICATIONS

Boardman, E.A., et al., "Deep Ultraviolet (UVC) Laser for Sterilisation and Fluorescence Applications," Sharp Laboratories of Europe, Ltd., 2012, https://corporate.jp.sharp/rd/n36/pdf/104_08.pdf, Last Visited on Aug. 16, 2023 (5 Pages).

*Primary Examiner* — Tracie Y Green

(57) ABSTRACT

The present invention relates to a light generating device (1) configured to generate device light (9), the light generating device comprising a first laser light source (2), a first frequency doubling element (4), a first luminescent element (6), and a light exit window (7). The first laser light source (2) is arranged for generating first laser light (3) being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm. The first laser light (3) comprises at least a first portion (3') and a second portion (3"). The first frequency doubling element (4) is arranged for converting at least a portion of the first portion (3') of the first laser light (3) emitted by the first laser light source (2) into a first frequency doubled light (5) having a third peak wavelength $\lambda_3$ selected from a spectral wavelength range from 190 to 245 nm. The first luminescent element (6) comprises a first (Continued)

luminescent material configured to convert at least a portion of the second portion (3") of the first laser light (3) into a first converted light (8) having a fourth peak wavelength $\lambda_4$ in one or more of (a) the green spectral wavelength range and (b) the yellow spectral wavelength range. The light exit window (7) is arranged to release the device light (9) comprising the first frequency doubled light (5) and the first converted light (8).

15 Claims, 2 Drawing Sheets

(51) Int. Cl.
*A61L 2/10* (2006.01)
*A61L 2/26* (2006.01)
*A61L 9/20* (2006.01)
*F21V 13/08* (2006.01)
*H05B 45/20* (2020.01)
*F21Y 113/00* (2016.01)
*F21Y 113/13* (2016.01)
*F21Y 115/30* (2016.01)

(52) U.S. Cl.
CPC ........ *A61L 2202/11* (2013.01); *F21Y 2113/13* (2016.08); *F21Y 2113/30* (2023.05); *F21Y 2115/30* (2016.08)

(56) References Cited

U.S. PATENT DOCUMENTS

| | | |
|---|---|---|
| 2013/0100977 A1 | 4/2013 | Smeeton et al. |
| 2018/0106460 A1* | 4/2018 | Van Bommel ........ F21V 29/502 |
| 2020/0073199 A1 | 3/2020 | Lin et al. |
| 2020/0244044 A1* | 7/2020 | Ramer .................. H01S 5/0092 |

* cited by examiner

LIGHT GENERATING DEVICE HAVING IMPROVED PERFORMANCE FOR DISINFECTION AND GENERAL LIGHTING

CROSS-REFERENCE TO PRIOR APPLICATIONS

This application is the U.S. National Phase application under 35 U.S.C. § 371 of International Application No. PCT/EP2022/053464, filed on Feb. 14, 2022, which claims the benefit of European Patent Application No. 21157804.2, filed on Feb. 18, 2021. These applications are hereby incorporated by reference herein.

TECHNICAL FIELD

The present invention relates to a light generating device configured to generate device light, the light generating device comprising a first laser light source, a first frequency doubling element, a first luminescent element, and a light exit window. The present invention further relates to a luminaire or a lamp comprising the light generating device, and a method for operating the light generating device.

BACKGROUND

In view of the recent development in the world concerning the global pandemic, disinfection has become a topic of renewed interest as the demand for sterilization increases. One way of disinfecting involves the use of UV light. As a response to pathogenic outbreaks involving air- or water-borne microorganisms it would be beneficial to employ UV light for disinfecting air, objects, and water at locations where the transmission of such microorganisms is believed to occur.

Disinfecting luminaires are used to flood spaces such as a hospital rooms with UV-B (ultra-violet light of 280-315 nanometer (nm)) and UV-C (ultra-violet light of 200-280 nm) radiation for disinfection purposes. Such disinfecting luminaires require a relatively brief time, e.g. several minutes, to achieve adequate disinfection but require the room to be evacuated of people. Another type of disinfecting luminaire uses a fixed 405 nm violet light source to provide disinfection without evacuating people from the room. However, such luminaires may require hours to achieve adequate disinfection because their light is less effective at killing pathogens than UV-B and UV-C radiation and is dispersed over a wide area so the irradiance level is relatively low.

Another device for UV treatment of air and water is a mercury lamp. However, mercury lamps contain toxic material, tend to have short operating lifetimes, and long warm-up times and require high driving voltages. Furthermore, the UV light emitted from mercury lamps is emitted in a broad range of directions and from a relatively large area which means it cannot be efficiently focused into a small area or a collimated beam.

An alternative UV light source currently under development is the UV LED. The main drawbacks of using UV LEDs is the very poor performance at emission wavelengths shorter than 260 nm. Therefore, these devices are less suited for the applications described above which benefit from a light source with wavelength shorter than 260 nm.

In contrast to UV LEDs and Hg lamps, UV lasers potentially provide a monochromatic, coherent beam which can be efficiently collected into a collimated beam or focused into a small area. However, existing lasers with emission wavelengths shorter than 280 nm are very expensive components and are mainly designed for industrial use. Further, no laser diodes have been made with emission wavelength shorter than 280 nm.

A UV laser can be realized by frequency doubling a visible laser beam inside a suitable non-linear optical material (e.g. Beta-Barium Borate which is commonly known as BBO), as first reported in IEEE Journal of Quantum Electronics QE-22, No 7 (1986). The visible light is focused into the non-linear optical material and the light is frequency-doubled (FD) by the process of second harmonic generation (SHG). The SHG process converts the visible input light into light with wavelength half the wavelength of the input light.

Normally, disinfection by UV light sources is used under controlled conditions in areas where humans or animals are not present during ongoing disinfection, such as at surgery theaters or the like. However, the increased demand for germicidal activities may involve operating UV light sources in environments with human presence, thus introducing a risk for unintentional irradiation by UV light. Therefore, disinfecting light sources, in particular those involving UV light, should possess reliable safety features in order to avoid potential exposure of humans or animals to the harmful irradiation. One such a feature is combining the UV light source with a visible light source. Utilizing such an approach, the user will be notified of the presence of the UV irradiation whenever the visible light source is emitting light.

Several attempts have been made to implement the safety feature mentioned above, i.e. to combine UV light source with a visible light source. To this end, US 2013/0100977 discloses a laser device providing an ultraviolet laser beam and a visible laser beam. The laser device of US 2013/0100977 includes a semiconductor laser device (e.g. a laser diode) to generate visible laser light having wavelength in the range from 400 nm to 560 nm, which is coupled into a frequency doubling crystal taking the form of a single crystal thin film frequency-doubling waveguide structure. The single crystal thin film frequency-doubling waveguide converts a portion of the visible light emitted by the laser diode into ultraviolet light. An advantage of using a UV laser made by frequency doubling according to US 2013/0100977 is that the device can emit both the UV laser light and a portion of the visible laser light. The visible laser light beam is particularly useful from a safety point of view, since, unlike deep UV light, it is visible to the naked eye.

It is desirable to provide a light generating device that combines high safety level with improved optical properties, in particular high brightness. High brightness visible light sources are interesting e.g. for flashlights, microscopes, endoscopes, searchlights, and spotlights. Disinfection is desired to protect people from the spread of bacteria and viruses such as influenza or against the outbreak of novel viruses like the recent corona virus. Such a combination of high brightness and germicidal activity may thus be particularly advantageous in health care facilities.

SUMMARY OF INVENTION

The present invention thus provides a light generating device configured to generate device light, the light generating device comprising a first laser light source, a first frequency doubling element, a first luminescent element, and a light exit window.

The first laser light source is arranged for generating first laser light being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm. The first laser light source may be a semiconductor laser diode. Preferably, the first laser light source generates first laser light in the range of 405+/−3 nm, because it is safe and can also be effectively used for disinfection. It should be noted that since the wavelength of the first laser light is <690 nm, the first laser light source provides first laser light which contributes substantially to the white light.

The first laser light comprises at least a first portion and a second portion. Further, the first laser light may comprise a third portion. The first laser light may be split into the first portion, the second portion and optionally the third portion by means of a splitting optical element. The splitting optical element may be a reflective polarizer, a semitransparent specular reflector, a dichroic element, a polarizing beamsplitter, a diffractive optical element or combination thereof.

The first frequency doubling element is arranged for converting at least a portion of the first portion of the first laser light emitted by the first laser light source into a first frequency doubled light having a third peak wavelength $\lambda_3$ selected from a spectral wavelength range from 190 to 245 nm (second harmonic generation). Preferably, the entire first portion of the first laser light is converted to the first frequency doubled light. The portion of the first portion of the first laser light that has not been converted to the first frequency doubled light may exit through the light exit window thus forming a part of the device light. The peak wavelength of the first frequency doubled light is half the peak wavelength of the first portion of the first laser light. In other words, if the first laser light has peak wavelength $\lambda_1$, the frequency doubled light will have peak wavelength $\lambda_3=\lambda_1/2$. The frequency doubled light has properties similar to the properties of the first laser light. The first frequency doubling element may be a frequency doubling crystal comprising Beta-Barium Borate (BBO), potassium fluoroboratoberyllate, lithium tetraborate, lithium rubidium tetraborate or magnesium barium fluoride. The first frequency doubling element is preferably optically coupled to the first laser light source. Thus, both visible first laser light and ultraviolet first frequency doubled light laser beams are simultaneously emitted. By using both types of light the user of the light generating device will be notified about generation of invisible UV light when seeing visible emission, thus improving safety of the light generating device.

The light generating device according to the present invention may generate frequency doubling UV light having peak wavelength as short as 190 nm. In particular, the frequency doubled light may be UVC light having wavelength from 220 to 280 nm, UVB light having wavelength from 280 to 315 nm or UVA light having wavelength from 315 to 400 nm.

The first luminescent element comprises a first luminescent material configured to convert at least a portion of the second portion of the first laser light into a first converted light having a fourth peak wavelength $\lambda_4$ in one or more of (a) the green spectral wavelength range and (b) the yellow spectral wavelength range. By the term "green spectral wavelength range" is understood the range from 495 nm to 570 nm, and by the term "yellow spectral wavelength range" in understood the range from 570 nm to 590 nm. The fourth peak wavelength $\lambda_4$ may be the dominant wavelength. The term "dominant wavelength" is well known to the person skilled in the art and means the wavelength of the monochromatic stimulus that, when additively mixed in suitable proportions with the specified achromatic stimulus, matches the color stimulus considered. The first converted light may comprise a component having emission wavelength in the red spectrum.

The first luminescent material may be of the type $A_3B_5O_{12}$:Ce, wherein A comprises one or more of Y, La, Gd, Tb and Lu, and wherein B comprises one or more of Al, Ga, In and Sc. In particular, A comprises at least Y, and B comprises at least Al.

The second portion of the first laser light, i.e. the portion of the first laser light that has not been directed to the first frequency doubling element, is directed towards the first luminescent element, wherein at least a portion of the second portion of the first laser light is converted into a first converted light having an emission band having peak wavelengths in one or more of (a) the green spectral wavelength range and (b) the yellow spectral wavelength range.

Thus, the entire second portion of the first laser light may be converted into the first converted light. Alternatively, only a portion of the second portion of the first laser light may be converted into the first converted light. In this case, the light leaving the first luminescent element will comprise the first converted light and a portion of the second portion of the first laser light.

The light exit window of the light generating device of the present invention is arranged to release the device light comprising at least the first frequency doubled light and the first converted light. As mentioned above, the device light may consist of the first frequency doubled light and the first converted light if the entire second portion of the first laser light is converted into the first converted light by the first luminescent element. Preferably, the device light consists of the first frequency doubled light, the first converted light and the first laser light when only a portion of the second portion of the first laser light is converted by the first luminescent element.

Consequently, the light generating device according to the present invention generates the device light comprising both UV laser light in the form of the first frequency doubled light, and visible light in the form of the first converted light or a combination of the first converted light and the first laser light. Simultaneous emission of the UV and visible laser light ensures a safe operation of the light generating device, while providing the first converted light by means of the first luminescent element improves optical properties of the light generating device by providing high brightness.

Preferably, the first peak wavelength $\lambda_1$ and/or the second peak wavelength $\lambda_2$ of the first laser light may be in the range from 400 to 440 nm and the third peak wavelength $\lambda_3$ of the first frequency doubled light may consequently be in the range from 200 to 220 nm. Thus, the emitted UV laser light in the form of the first frequency doubled light will be in the rather safe UV-C range.

When the first laser light comprises a third portion as described above, the device light further comprises the third portion of the first laser light. In other words, the device light according to such an embodiment consists of the first frequency doubled light, the first converted light, and the third portion of the first laser light.

The third portion of the first laser light may have the first peak wavelength Xi and/or the second peak wavelength $\lambda_2$ in the range from 380 nm to 450 nm and providing germicidal properties to some extent. In particular, the third portion may have the first peak wavelength $\lambda_1$ and/or the second peak wavelength $\lambda_2$ in the range from 400 nm to 420 nm, preferably 405+/−3 nm. Further, the third portion of the first laser light may have the first peak wavelength $\lambda_1$ and/or the second peak wavelength $\lambda_2$ in the range from 450 nm to 495 nm, which added to the green/yellow spectra of the first converted light provides white or whitish light. The visible UV light will thus consist of the first converted light having a third peak wavelength $\lambda_3$ in the range from 495 nm to 590 nm, and the third portion of the first laser light having the first peak wavelength $\lambda_1$ and/or the second peak wavelength $\lambda_2$ in the range from 380 nm to 495 nm, thus providing visible laser light of high brightness accompanied by disinfecting UV laser light in the form of the first frequency doubled light.

The first luminescent element may comprise a second luminescent material arranged to convert a portion of the second portion of the first laser light into a second converted light having a fifth peak wavelength $\lambda_5$ in one or more of (a) a blue spectral wavelength range and (b) a red spectral wavelength range. Thus, a portion of the second portion of the first laser light may be converted into the first converted light by the first luminescent material, and another portion of the second portion of the first laser light may be converted into the second converted light having the fifth peak wavelength $\lambda_5$ in the range from 450 nm to 495 nm and/or in the range from 620 nm to 750 nm. As mentioned previously, the entire second portion of the first laser light may be converted into the first converted light and the second converted light. The device light emitted by the light generating device of the present invention will thus consist of the first frequency doubled light, the first converted light and the second converted light. Alternatively, only a portion of the second portion of the first laser light may be converted into the first converted light and the second converted light. The device light will thus consist of the first frequency doubled light, the first converted light, the second converted light and the first laser light. Thus, the visible laser light according to such an embodiment may be white light, since the first peak wavelength $\lambda_1$ and/or the second peak wavelength $\lambda_2$ of the first laser light is in the range from 380 nm to 495 nm, the first converted light has a third peak wavelength $\lambda_3$ in the range from 495 nm to 590 nm, and the second converted light may have a fifth peak wavelength $\lambda_5$ in the range from 620 nm to 750 nm.

The light generating device of the present invention may comprise a second luminescent element comprising a third luminescent material arranged to convert a portion of the second portion of the first laser light into a third converted light having a sixth peak wavelength $\lambda_6$ in one or more of (a) a blue spectral wavelength range and (b) a red spectral wavelength range. The third luminescent material may be the same as the second luminescent material or may be different from the second luminescent material. In analogy with the above, the entire second portion of the first laser light may be converted into the first converted light, the second converted light and the third converted light. The device light emitted by the light generating device according to such an embodiment will thus consist of the first frequency doubled light, the first converted light, the second converted light and the third converted light. The visible UV laser light may thus even in this case be white light, since green and/or yellow, blue, and red spectral wavelength ranges, respectively, may be combined.

Alternatively, only a portion of the second portion of the first laser light may be converted into the first converted light, the second converted light and the third converted light. The device light will thus consist of the first frequency doubled light, the first converted light, the second converted light, the third converted light and the first laser light. Thus, the visible laser light according to such an embodiment may be white light, since green and/or yellow, blue, red, and violet spectral wavelength ranges, respectively, may be combined.

In a particularly preferred embodiment, the second converted light and/or the third converted light has the fifth peak wavelength $\lambda_5$ and/or the six peak wavelength $\lambda_6$ in the blue spectral wavelength range, the first laser light has the first peak wavelength $\lambda_1$ and/or the second peak wavelength $\lambda_2$ in the range from 400 to 420 nm, and the first frequency doubled light has the third peak wavelength $\lambda_3$ in the range from 200 to 210 nm.

The light generating device according to the present invention may further comprise a second laser light source being arranged for generating second laser light being at least one of blue laser light having the seventh peak wavelength $\lambda_7$ in the range from 420 to 490 nm and red laser light. The device light may thus comprise the frequency doubled light, the first laser light, the second laser light, the first converted light, the second converted light and the third converted light. Preferably, the first laser light, the second laser light, the first converted light, the second converted light and the third converted light have different peak wavelength ranges, such that the device light comprises bright white laser light accompanied by disinfecting UV laser light.

The light generating device may further comprise a red phosphor. A suitable red phosphor material may be selected from the groups consisting of rare-earth activated and non-rare earth activated fluorides, nitrides, borates, phosphates, oxides, vanadates, silicates, molybdates, tungstates and sulphides. The red phosphor material may be pumped by the first laser light and/or first converted light and/or second laser light.

The light generating device of the present invention may further comprise a second frequency doubling element generating a second frequency doubled light. The second frequency doubled light preferably has a peak wavelength different from the peak wavelength of the first frequency doubled light, meaning that the second frequency doubling element receives a light having different peak wavelength from the first peak wavelength $\lambda_1$ and/or the second peak wavelength $\lambda_2$ of the first laser light. The second frequency doubling element may receive a second laser light originating from a second laser light source or may be preceded by an optical element converting the first laser light to a light having different peak wavelength, such as a second luminescent element.

The light generating device according to the present invention may comprise a plurality of laser light sources and/or a plurality of frequency doubling elements. The term "plurality" in the context of the present invention is to be understood as "two or more". Preferably, each of the plurality of the laser light sources generates a laser light having peak wavelength range being different from the peak wavelength range of the laser light generated by the other laser light sources. For instance, laser light sources arranged for generating green laser light having a peak wavelength of from 495 to 570 nm and/or yellow laser light having a peak wavelength of from 570 to 590 nm may be used, such that optical properties of the visible laser light, e.g. brightness and quality, are improved. In such an embodiment, the device light will comprise a plurality of components, comprising laser light originating from the different laser light sources, frequency doubled light being converted by the plurality of frequency doubling elements as well as converted light originating from the at least one luminescent element. Each component of the device light will have a peak wavelength range being different from the peak wavelength range of the other components, thus providing visible white laser light of high brightness.

The device light may be white light having a color temperature in the range from 2000 to 10000 K and a color rendering index (CRI) of at least 70. Preferably, the CRI is at least 80, more preferably at least 85, most preferably at least 90. The color temperature may be from 2000 to 8000 K.

The light generating device according to the present invention may further comprise a filtering element arranged downstream of the first frequency doubling element for filtering a portion of the first frequency doubled light. The filtering element may be any optical element having spectral filtering function, such as a dispersion prism, a diffractive optical element, an optical filter or a combination thereof. Preferably, the filtering element is arranged immediately after the first frequency doubling element. The term "immediately after" means that no other components are arranged between the first frequency doubling element and the filter. Alternatively, other optical elements such as a resonator mirror, a diffractive grating or the like may be arranged between the first frequency doubling element and the filtering element. If plurality of frequency doubling elements is present, a filtering element may be arranged downstream each frequency doubling element.

The light generating device of the present invention may further comprise a mixing optical element arranged upstream of the light exit window configured to combine at least the first frequency doubled light and the first converted light. Indeed, the mixing element may be used for combining all the components of the device light discussed above, such as the first laser light, the second laser light, the second frequency doubled light, the second converted light or the like. Preferably, the mixing optical element is arranged immediately before the light exit window. The term "immediately before" means that no other components are arranged between the mixing optical element and the light exit window.

The light generating device according to the present invention may further comprise one or more sensors arranged to sense the first frequency doubled light and/or the first converted light and generate one or more signals. Further, the light generating device may comprise a controller arranged to receive the one or more signals and to control the light generating device based on the one or more signals.

The present invention further relates to a luminaire or a lamp comprising the light generating device as described above. The luminaire or the lamp of the present invention provides visible laser light of high brightness and quality, being accompanied by the UV laser light that may be used for disinfection purposes. The luminaire or the lamp of the present invention possesses high safety, since the user is aware of the UV irradiation once visible light is emitted. The luminaire or the lamp of the present invention is particularly suitable for use in health care facilities, e.g. in operation theaters, wherein lighting devices providing visible light of good quality along with light having germicidal properties are highly sought after.

Finally, the present invention relates to a method for operating a light generating device described above and configured to generate device light. The light generating device comprises a first laser light source arranged for generating first laser light being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm, a first frequency doubling element, a first luminescent element comprising a first luminescent material, and a light exit window. The features of the light generating device have been described in detail above. The method of the present invention comprises the steps of:

a) splitting the first laser light into at least a first portion and a second portion;
b) converting at least a portion of the first portion of the first laser light emitted by the first laser light source into a first frequency doubled light having a third peak wavelength $\lambda_3$ selected from a spectral wavelength range from 190 to 245 nm by means of the first frequency doubling element;
c) converting at least a portion of the second portion of the first laser light into a first converted light by means of the first luminescent element, wherein the first converted light has a fourth peak wavelength $\lambda_4$ in one or more of (a) the green spectral wavelength range and (b) the yellow spectral wavelength range;
d) releasing the device light comprising at least the first frequency doubled light and the first converted light through the light exit window.

When the light generating device comprises a light mixing element arranged upstream of the light exit window, the method may further comprise the step of:

c') mixing the frequency doubled light and at least the first converted light.

If present, step c') occurs between step c) and step d).

As mentioned above, the light generating device may comprise a sensor arranged to sense the first frequency doubled light and/or the first converted light and generate a signal. Further, the light generating device may comprise a controller arranged to receive the signal and to control the light generating device based on the signal. In this case, the method may comprise the steps of:

e) generating at least one signal by means of the sensor,
f) receiving the at least one signal by the controller;
g) controlling the light generating device based of the at least one signal.

BRIEF DESCRIPTION OF THE DRAWINGS

Embodiments of the invention will now be described by way of example with reference to the accompanying drawings, of which.

Figure 1:
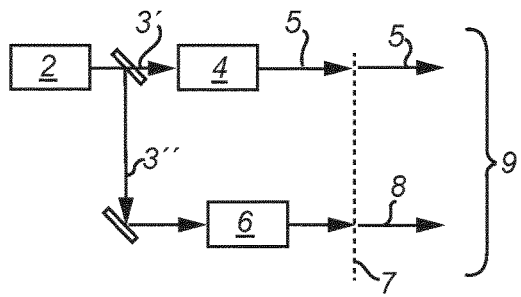
FIGS. 1-5 illustrate different embodiments of the light generating device according to the present invention.

All the figures are schematic, not necessarily to scale, and generally only show parts which are necessary in order to elucidate embodiments of the present invention, wherein other parts may be omitted or merely suggested.

DETAILED DESCRIPTION

The present invention will now be described hereinafter with reference to the accompanying drawings, in which exemplifying embodiments of the present invention are shown. The present invention may, however, be embodied in many different forms and should not be construed as limited to the embodiments of the present invention set forth herein; rather, these embodiments of the present invention are provided by way of example so that this disclosure will convey the scope of the invention to those skilled in the art.

In the drawings, identical reference numerals denote the same or similar components having a same or similar function, unless specifically stated otherwise.

FIG. 1 depicts a light generating device 1 configured to generate device light 9, the light generating device comprising a first laser light source 2, a first frequency doubling element 4, a first luminescent element 6, and a light exit window 7.

The first laser light source 2 is arranged for generating first laser light 3 being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm. The first laser light 3 comprises at least a first portion 3' and a second portion 3".

The first frequency doubling element 4 is arranged for converting the first portion 3' of the first laser light 3 emitted by the first laser light source 2 into a first frequency doubled light 5 having a third peak wavelength $\lambda_3$ selected from a spectral wavelength range from 190 to 245 nm (second harmonic generation). The peak wavelength of the first frequency doubled light 5 is half the peak wavelength of the first portion 3' of the first laser light 3. The first frequency doubling element 2 is optically coupled to the first laser light source 2. By using both types of light the user of the light generating device 1 will be notified about generation of invisible UV light 5 when seeing visible emission 8, thus improving safety of the light generating device 1.

The first luminescent element 6 comprises a first luminescent material configured to convert the second portion 3" of the first laser light 3 into a first converted light 8 having a fourth peak wavelength $\lambda_4$ in one or more of (a) the green spectral wavelength range and (b) the yellow spectral wavelength range.

The light exit window 7 of the light generating device 1 of the present invention is arranged to release the device light 9 comprising the first frequency doubled light and the first converted light 8.

Consequently, the light generating device 1 according to the embodiment shown in FIG. 1 generates the device light 9 comprising both UV laser light in the form of the first frequency doubled light 5, and visible light in the form of the first converted light 8. Simultaneous emission of the UV and visible laser light ensures a safe operation of the light generating device 1, while providing the first converted light 8 by means of the first luminescent element 6 improves optical properties of the light generating device 1 by providing high brightness.

Figure 2:
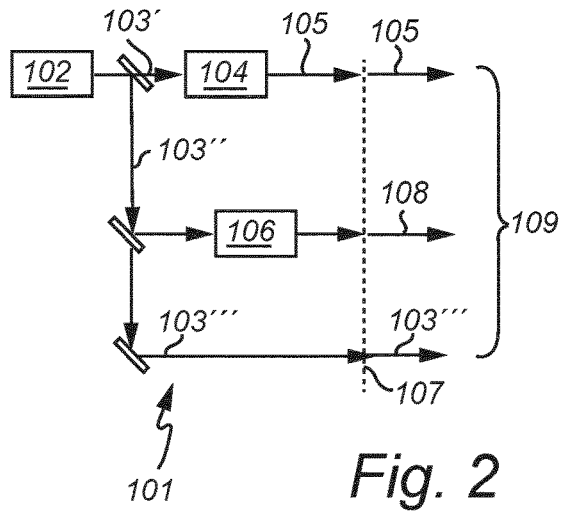

As depicted in FIG. 2, a light generating device 101 comprises a first laser light source 102, a first frequency doubling element 104, a first luminescent element 106, and a light exit window 107.

The first laser light source 102 is arranged for generating first laser light 103 being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm. The first laser light 103 comprises a first portion 103', a second portion 3", and a third portion 103". The first frequency doubling element 104 is arranged for converting the first portion 103' of the first laser light 103 emitted by the first laser light source 102 into a first frequency doubled light 105 having a third peak wavelength $\lambda_3$ selected from a spectral wavelength range from 190 to 245 nm (second harmonic generation). The peak wavelength of the first frequency doubled light 105 is half the peak wavelength of the first portion 103' of the first laser light 103. The first frequency doubling element 102 is optically coupled to the first laser light source 102.

The first luminescent element 106 comprises a first luminescent material configured to convert the second portion 103" of the first laser light 103 into a first converted light 108 having a fourth peak wavelength $\lambda_4$ in one or more of (a) the green spectral wavelength range and (b) the yellow spectral wavelength range.

The light exit window 107 of the light generating device 101 of the present invention is arranged to release the device light 109 consisting of the first frequency doubled light 105, the first converted light 108, and the third portion of the first laser light 103".

Figure 3:
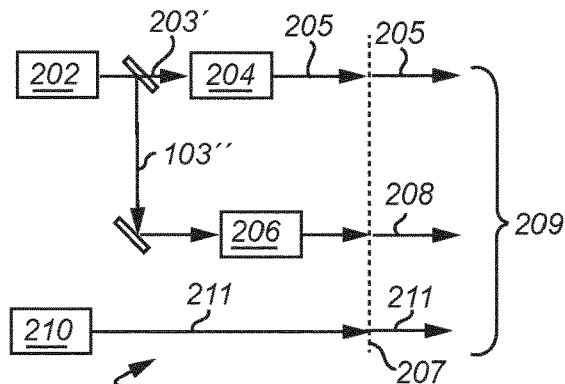

The embodiment depicted in FIG. 3 is similar to the one shown in FIG. 1. As may be seen in FIG. 3, the light generating device 201 comprises a second laser light source 210 being arranged for generating second laser light 211 being at least one of blue laser light having the seventh peak wavelength $\lambda_7$ in the range from 420 to 490 nm and red laser light. The device light 209 thus comprises the frequency doubled light 205, the second laser light 211 and the first converted light 208.

Figure 4:
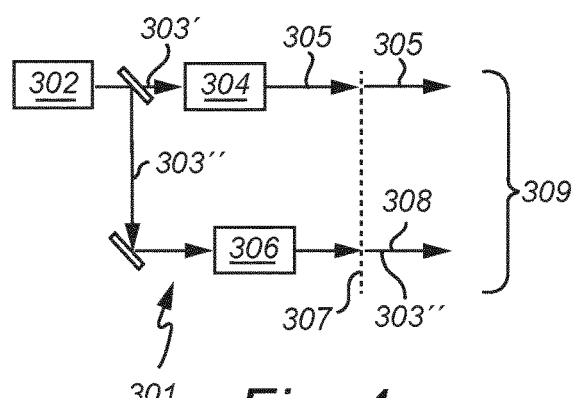

FIG. 4 illustrates yet another embodiment of the present invention. As may be seen in FIG. 4, the light generating device 301 is similar to the one shown in FIG. 1. However, only a portion of the second portion 303" of the first laser light 303 is converted into the first converted light 308. The device light 309 will thus consist of the first frequency doubled light 305, the first converted light 308 and the second portion 303" of the first laser light 303.

Figure 5:
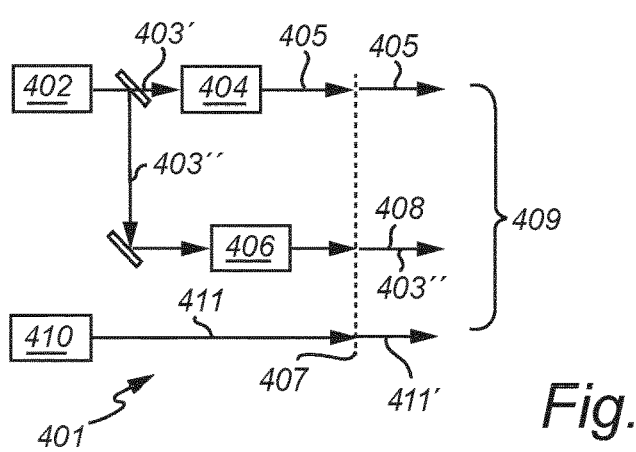
Figure 6:
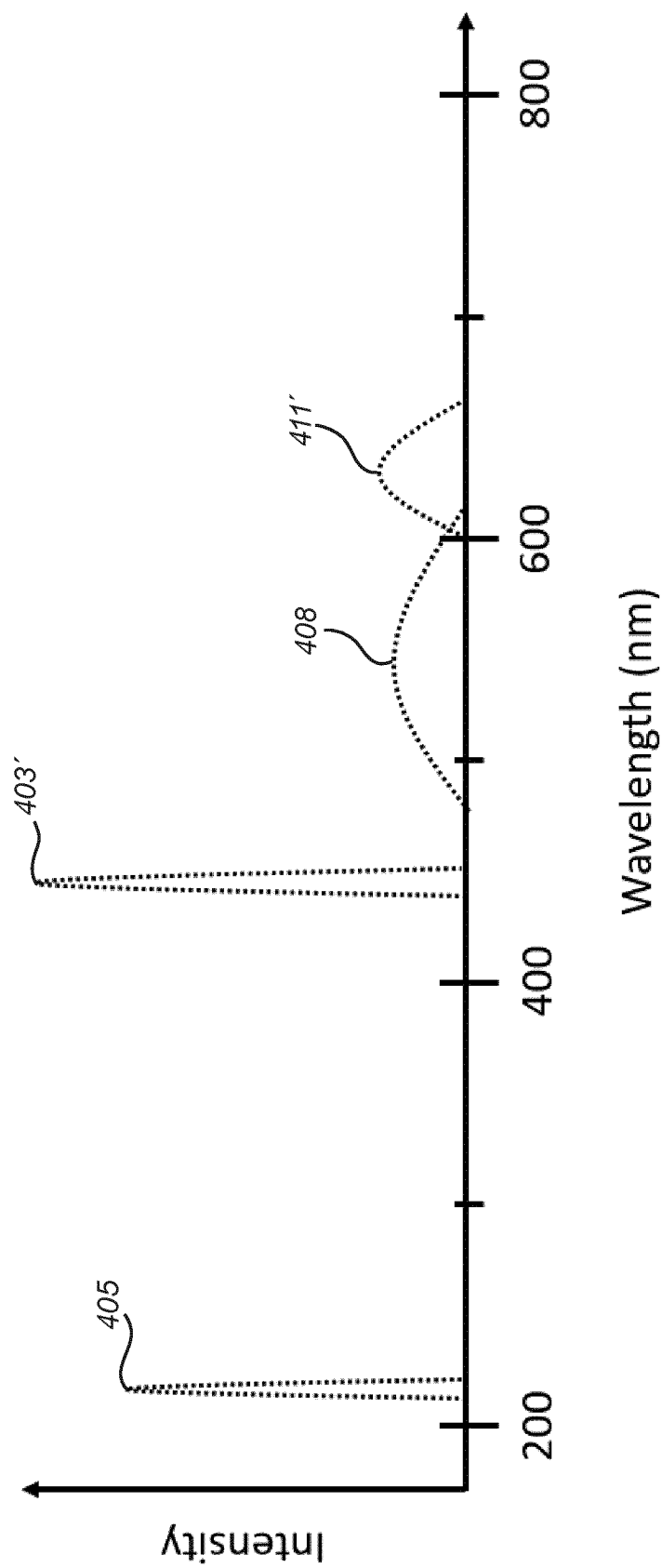
FIG. 6 illustrates different components of the device light generated by the light generating device depicted in FIG. 5.

FIG. 5 illustrates an embodiment similar to the one shown in FIG. 4, wherein a second laser light source 410 is arranged for providing a second laser light 411. The light generating device 401 further a red phosphor material (not shown) being pumped by the second laser light 411 thus providing red phosphor emission 411'. In the embodiment depicted in FIG. 5, the device light 409 thus consists of the first frequency doubled light 405, the first converted light 408, the second portion 403" of the first laser light 403, and the red phosphor emission 411'. FIG. 6 illustrates these four components of the device light 409.

Although the present invention has been described with reference to various embodiments, those skilled in the art will recognize that changes may be made without departing from the scope of the invention. It is intended that the detailed description be regarded as illustrative and that the appended claims including all the equivalents are intended to define the scope of the invention. While the present invention has been illustrated in the appended drawings and the foregoing description, such illustration is to be considered illustrative or exemplifying and not restrictive; the present invention is not limited to the disclosed embodiments. Other variations to the disclosed embodiments can be understood and effected by those skilled in the art in practicing the claimed invention, from a study of the drawings, the disclosure, and the appended claims. In the appended claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light generating device configured to generate device light, said light generating device comprising a first laser light source, a first frequency doubling element, a first luminescent element, and a light exit window, wherein:

said first laser light source is arranged for generating first laser light being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm, said first laser light comprising at least a first portion and a second portion;

said first frequency doubling element is arranged for converting at least a portion of said first portion of said first laser light emitted by said first laser light source into a first frequency doubled light having a third peak wavelength $\lambda_3$ selected from a spectral wavelength range from 190 to 245 nm;

said first luminescent element comprises a first luminescent material configured to convert at least a portion of said second portion of said first laser light into a first converted light having a fourth peak wavelength $\lambda_4$ in one or more of (a) the green spectral wavelength range and (b) the yellow spectral wavelength range; and said light exit window is arranged to release said device light comprising at least said first frequency doubled light and said first converted light.

2. The light generating device according to claim 1, wherein said at least one of said first peak wavelength $\lambda_1$ and said second peak wavelength $\lambda_2$ of said first laser light is selected from a spectral wavelength range from 400 to 440 nm and said third peak wavelength $\lambda_3$ of said first frequency doubled light is selected from a spectral wavelength range from 200 to 220 nm.

3. The light generating device according to claim 1, wherein said first laser light comprises a third portion and wherein said device light further comprises said third portion of said first laser light.

4. The light generating device according to claim 1, wherein said first luminescent element comprises a second luminescent material arranged to convert a portion of said second portion of said first laser light into a second converted light having an emission band having wavelengths in one or more of (a) a blue spectral wavelength range and (b) a red spectral wavelength range, and wherein said device light further comprises said second converted light.

5. The light generating device according to claim 1, wherein said light generating device comprises a second luminescent element comprising a third luminescent material arranged to convert a portion of said second portion of said first laser light into a third converted light having an emission band having wavelengths in one or more of (a) a blue spectral wavelength range and (b) a red spectral wavelength range, and wherein said device light further comprises said third converted light.

6. The light generating device according to claim 4, wherein said second converted light and/or said third converted light has an emission band having a peak wavelength in the blue spectral wavelength range, and wherein said at least one of said first peak wavelength $\lambda_1$ and said second peak wavelength $\lambda_2$ of said first laser light is selected from a spectral wavelength range from 400 to 420 nm and said third peak wavelength $\lambda_3$ of said first frequency doubled light is selected from a spectral wavelength range from 200 to 210 nm.

7. The light generating device according to claim 1, wherein said first luminescent material is of the type $A_3B_5O_{12}$:Ce, wherein A comprises one or more of Y, La, Gd, Tb and Lu, and wherein B comprises one or more of Al, Ga, In and Sc.

8. The light generating device according to claim 1, wherein said light generating device further comprises a second laser light source being arranged for generating second laser being at least one of blue laser light having a wavelength of from 420 to 490 nm and red laser light.

9. The light generating device according to claim 1, wherein said light generating device comprises a splitting optical element arranged for splitting said first laser light into said first and said second portion.

10. The light generating device according to claim 1, wherein said light generating device further comprises a filtering element arranged downstream of said first frequency doubling element for filtering a portion of said first frequency doubled light.

11. The light generating device according to claim 1, wherein said light generating device further comprises a mixing optical element arranged upstream of said light exit window configured to combine at least said first frequency doubled light and said first converted light.

12. The light generating device according to claim 1, wherein said light generating device further comprises one or more sensors arranged to sense the first frequency doubled light and/or the converted light and generate a signal, and a controller arranged to receive said one or more signals and to control said light generating device based on said one or more signals.

13. The light generating device according to claim 1, wherein said light generating device further comprises a second frequency doubling element generating a second frequency doubled light having a peak wavelength different from the peak wavelength of said first frequency doubled light.

14. A luminaire or a lamp comprising the light generating device according to claim 1.

15. A method for operating a light generating device configured to generate device light, said light generating device comprising a first laser light source arranged for generating first laser light being at least one of violet laser light having a first peak wavelength $\lambda_1$ selected from a spectral wavelength range from 380 to 420 nm and blue laser light having a second peak wavelength $\lambda_2$ selected from a spectral wavelength range from 420 to 490 nm, a first frequency doubling element, a first luminescent element comprising a first luminescent material, and a light exit window, said method comprising the steps of:

a) splitting said first laser light into at least a first portion and a second portion;

b) converting at least a portion of said first portion of said first laser light emitted by said first laser light source into a first frequency doubled light having a third peak wavelength $\lambda_3$ selected from a spectral wavelength range from 190 to 245 nm by means of said first frequency doubling element;

c) converting at least a portion of said second portion of said first laser light into a first converted light by means of said first luminescent element, wherein said first converted light has a fourth peak wavelength $\lambda_4$ in one or more of (a) the green spectral wavelength range and (b) the yellow spectral wavelength range;

d) releasing said device light comprising at least said first frequency doubled light and said first converted light through said light exit window.

* * * * *